(12) United States Patent
Matsumoto et al.

(10) Patent No.: US 6,369,050 B1
(45) Date of Patent: Apr. 9, 2002

(54) ANTIBACTERIAL AGENTS

(75) Inventors: Yoshimi Matsumoto, Souraku-gun; Shuichi Tawara, Kawanishi; Hitoshi Nishio, Toyonaka; Takashi Harimoto, Kobe; Ryoji Sekiyama, Ikeda, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/647,925

(22) PCT Filed: Apr. 9, 1999

(86) PCT No.: PCT/JP99/01924

§ 371 Date: Nov. 17, 2000

§ 102(e) Date: Nov. 17, 2000

(87) PCT Pub. No.: WO99/52530

PCT Pub. Date: Oct. 21, 1999

(30) Foreign Application Priority Data

Apr. 14, 1998 (JP) .......................................... 10-103148

(51) Int. Cl.⁷ .......................................... A61K 31/395
(52) U.S. Cl. .................... 514/210.05; 424/114
(58) Field of Search ...................... 514/210.05; 424/114

(56) References Cited

FOREIGN PATENT DOCUMENTS

| JP | 50-052219 | 5/1975 |
| JP | 52-064432 | 5/1977 |

OTHER PUBLICATIONS

CA112:115608, Mine et al, Chemotherapy, 37 (Suppl. 2), 100–21, 1989, abstract.*
CA112:111596, Mine et al, Chemotherapy, 37 (Suppl. 2), 145–53, 1989, abstract.*

Y. Matsumoto, Chemotherapy, vol. 44, pp. 6–9, "Combination Cefixime/Amoxicillin Against Penicillin–Resistant *Streptocococcus Pneumoniae* Infection," Sep. 1998.
Y. Yokota, et al., J. Drug Dev., vol. 6, pp. 5–9, "Antibacterial Activity of Cefixime in Combination with Other Antimocrobial Agents Against Penicillin–G–Resistant *Streptococcus Pneumoniae*," 1993.
B. Cassinat, et al., Journal of Antimicrobial Chemotherapy, Vo. 34, pp. 785–790, "Comparison of Antibiotic Combinations Against Penicillin–Resistant Pneumococci," 1994.
W. H. Traub, et al., Chemotherapy, vol. 43, pp. 159–167, "Susceptibility of Moraxella Catarrhalis To 21 Antimicrobial Drugs: Validity of Current NCCLS Criteria for the Interpretation of Agar Disk Diffusion Antibiograms," 1997.
A. L. Barry, Eur. J. Clin. Microbiol. Infect. Dis., vol. 11, pp. 867–869, "In Vitro potency of Nine Orally Administered Antimicrobial Agents Against Three Respiratory Tract Pathogens," 1992.
R. N. Jones, et al., Diagn Microbiol. Infect. Dis., vol. 31, pp. 373–376, "Combinations of Orally Administered β–Lactams to Maximize Spectrum and Activity Against Drug–Resistant Respiratory Tract Pathogens: I. Synergy Studies of Amoxicillin and Cefixime With *Streptococcus Pneumoniae*," 1998.

* cited by examiner

*Primary Examiner*—Rebecca Cook
(74) *Attorney, Agent, or Firm*—Oblon, Spivak, McClelland, Maier & Neustadt, P.C.

(57) ABSTRACT

The invention provides an antimicrobial agent capable of producing an excellent effect in the prevention or treatment of bacteria of two or more genera selected from among Streptococcus, Moraxella, Haemophilus, Klebsiella and the like. The agent comprises a penicillin antibiotic, in particular amoxicillin, and a cephem antibiotic, in particular cefixime or cefdinir. The antimicrobial agent of the invention is administered in the form of a mixed preparation containing both or in the form of individual preparations respectively containing them for combined administration.

4 Claims, 2 Drawing Sheets

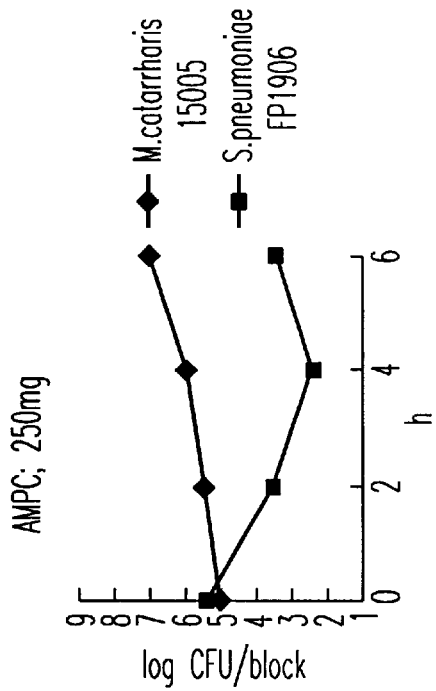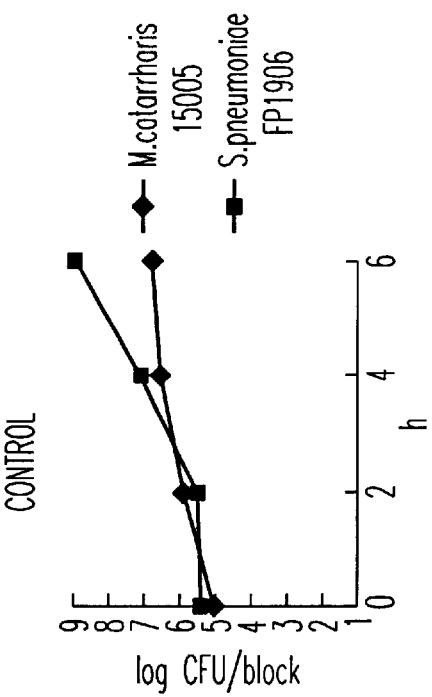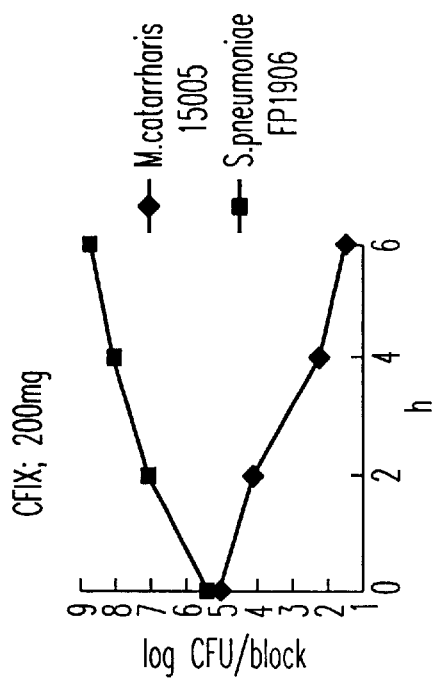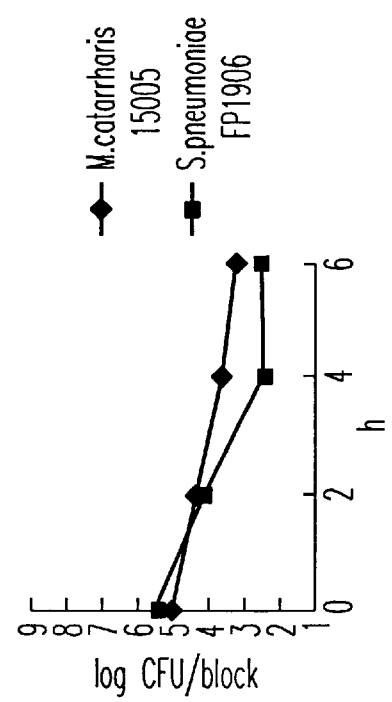

ANTIBACTERIAL AGENTS

This is a 371 of PCT/JP 99/01924 filed Apr. 9, 1999.

TECHNICAL FIELD

This invention relates to an antimicrobial agent which comprises a penicillin antibiotic, in particular amoxicillin, and a cephem antibiotic, in particular cefixime or cefdinir, and which is suited for use in the prevention or treatment of respiratory infections and mixed respiratory infections. The invention is utilized in the field of medicine.

BACKGROUND ART

Cefixime (hereinafter sometimes referred to as "CFIX") and cefdinir (hereinafter sometimes referred to as "CFDN") are oral cephem antibiotics, show a broad antibacterial spectrum against gram-positive and gram-negataive bacteria, and are in wide use. However, they are not very effective against the penicillin G-resistant pneumococcus belonging to the genus Streptococcus (*Streptococcus pneumoniae*).

On the other hand, amoxicillin (hereinafter sometimes referred to as "AMPC") is a synthetic oral penicillin, which is relatively effective against the above-mentioned pneumococcus but not so effective against gram-negative bacteria, in particular bacteria belonging to the genus Moraxella, Haemophilus or Klebsiella.

It is known that the combined use of CFIX and AMPC shows a synergistic effect against penicillin G-resistant *Streptococcus pneumoniae* and that said combined use is effective against mixed infection with penicillin G-resistant *Streptococcus pneumoniae* and *Haemophilus influenzae* [J. Drug Dev., 1993, 6 (Suppl. 1), 5–9].

Furthermore, it is also known that the combined use of CFDN and AMPC shows a synergistic effect against enterococcal infections (Japanese Kokai Tokkyo Koho H04-29930).

Bacteria belonging to the genus Streptococcus, Moraxella, Haemophilus or Klebsiella, for example *Streptococcus pneumoniae*, *Moraxella catarrhalis*, *Haemophilus influenzae* and *Klebsiella pneumoniae*, are main factors causative of respiratory infections. In some cases, patients are infected with only one of these bacteria and, in other cases, mixedly infected with two or more of these bacteria.

Mixed infections caused by these bacteria require urgent treatment. Since, however, a complicated procedure is required for the identification of causative bacteria, one drug having a broad antibacterial spectrum is administered prior to the identification of causative bacteria. However, among oral drugs, no one is sufficiently effective upon single drug administration. In cases where the effect is unsatisfactory, another drug is further administered in many cases after the lapse of a certain period of time.

However, by such conventional methods, it is difficult to obtain a complete cure at a stage where the symptoms of a respiratory infection are not so severe yet, so that aggravation of symptoms may result in some cases, making administration of an injection or hospitalization necessary and increasing the drug and medical expenses.

DISCLOSURE OF INVENTION

The inventors of this invention found that the combined use of a penicillin antibiotic, in particular AMPC, and a cephem antibiotic, in particular CFIX or CFDN, shows a synergistic effect against not only single infections but also mixed infections with the bacteria mentioned above and said combined use provides an antimicrobial agent useful in the prevention and treatment of respiratory infections with one bacterial species and of mixed respiratory infections with a plurality of bacteria.

BEST MODES FOR CARRYING OUT THE INVENTION

The bacteria against which the combined use of a penicillin antibiotic and a cephem antibiotic according to this invention produces a synergistic effect are bacteria causative of respiratory infections and, as examples, there may be mentioned bacteria of the genus Streptococcus (e.g. penicillin G-resistant or sensitive *Streptococcus pneumoniae* etc.), bacteria of the genus Moraxella (e.g. *Moraxella catarrhalis* etc.), bacteria of the genus Haemophilus (e.g. *Haemophilus influenzae* etc.) and bacteria of the genus Klebsiella (e.g. *Klebsiella pneumoniae* etc.).

The antimicrobial agent of this invention is effective not only against single infections with these bacteria but also against mixed respiratory infections with two or more bacteria belonging to two or more different genera selected from these and other genera.

In particular, said agent is useful in treating mixed respiratory infections with bacteria of the genus Streptococcus (in particular penicillin G-resistant *Streptococcus pneumoniae*) and bacteria belonging to another one of the genera mentioned above.

The (mixed) respiratory infections against which the antimicrobial agent of this invention is effective include, among others, otitis media, sinusitis, bronchitis, pneumonia and the like.

The penicillin antibiotic to be used in the antimicrobial agent of this invention includes, among others, amoxicillin, ciclacillin, talampicillin, ampicillin, hetacillin, flucloxacillin, dicloxacillin, cloxacillin, oxacillin, bacampicillin and lenampicillin, and salts thereof. Preferred among them is amoxicillin.

The cephem antibiotic includes, among others, cefixime, cefdinir, cephalexin, cephradine, cefatrizine, cefaclor, cefroxadine, cefadroxil, cefetametpivoxil, cefotiamhexetil, cefditrenpivoxil, ceftibuten, cefteram pivoxil, cefpodoxime proxetil, cefcamate pivoxil, cefprozil and cefuroxime axetil, and salts thereof. Preferred among them are cefixime and cefdinir. Cefixime is more preferred.

As the salts of such penicillin and cefem antibiotics, there may be mentioned, for example, alkali metal salts such as sodium salt and potassium salt, alkaline earth metal salts such as calcium salt and magnesium salt, salts with inorganic or organic bases, such as ammonium salt, ethanolamine salt, triethylamine salt and cyclohexylamine salt, acid addition salts with inorganic or organic acids, such as acetic acid salt, trifluoroacetic acid salt, lactic acid salt, maleic acid salt, fumaric acid salt, tartaric acid salt, citric acid salt, methanesulfonic acid salt, hydrochloride, sulfate, nitrate and phosphate, and the like.

The penicillin and cephem antibiotics and salts thereof include hydrates thereof (e.g. trihydrate) as well.

In the antimicrobial agent of this invention, the mixing ratio or use ratio between the penicillin antibiotic and cephem antibiotic is to be selected considering the antibiotics to be combined, the kind or kinds of causative bacteria, the severity of infection and other factors. Generally, said ratio is adequately selected within the range of 20:1 to 1:5 by weight, preferably 10:1 to 1:2, more preferably 5:1 to 1:1.

This invention consists in using a penicillin antibiotic and a cephem antibiotic combinedly. The penicillin antibiotic and cephem antibiotic may be administered either in the form of a mixed preparation containing both blended therein or simultaneously as individual single dosage forms containing them separately.

The antimicrobial agent of this invention, whether it is in the form of a mixed preparation or separate preparations, can be orally administered in the form of conventional dosage forms such as capsules, microcapsules, tablets, granules, fine granules, powders, troches or pills.

These dosage forms can be produced by conventional methods using excipients such as sucrose, starch, mannitol, sorbitol, lactose, glucose, cellulose, microcrystalline cellulose, calcium phosphate and calcium carbonate, binders such as cellulose, methylcellulose, hydroxypropylcellulose, hydroxypropylmethylcellulose, hydroxymethylcellulose, polyvinylpyrrolidone, polypropylpyrrolidone, gelatin, gum arabic, polyethylene glycol, sucrose and starch, disintegrants such as starch, carboxymethylcellulose, low-substituted hydroxypropylcellulose, sodium hydrogen carbonate, calcium phosphate and calcium citrate, lubricants such as magnesium stearate, light anhydrous silicic acid, talc and sodium lauryl sulfate, flavorings such as citric acid, menthol, glycine and orange powder, preservatives such as sodium benzoate, sodium hydrogen sulfite, methylparaben and propylparaben, stabilizers such as citric acid, sodium citrate and acetic acid, and other common organic and inorganic carriers conventionally used in dosage form production.

In cases where separate preparations (e.g. capsules, tablets, etc.) containing the respective antibiotics are used, they may be packaged on separate sheets. It is convenient for the use by patients, however, to prepare kits by packaging a penicillin antibiotic (e.g. 5 capsules) on one side and a cephem antibiotic (e.g. 5 capsules) on the other side of one and the same sheet (e.g. press through package (PTP) sheet or strip packaging sheet), or by packaging the doses of both preparations for one course of treatment (1 day to 2 weeks), for instance, on one and the same sheet.

In cases where the respective preparations are in the form of fine granules or the like, it is convenient for the use by patients to package the doses of the penicillin antibiotic and cephem antibiotic for one course of treatment alternatingly (e.g. per single dose of each) in the form of a folded packaging sheet, or prepare kits by placing the containers containing the respective fine granule preparations in one and the same case, for instance. These packaging procedures can be performed in the conventional manner.

The amounts of the active ingredients contained in this antimicrobial agent, namely the total dose of the penicillin antibiotic and cephem antibiotic, should be sufficient to produce the desired preventive effect or the desired therapeutic effect on the disease process and condition. The dose for patients may vary depending on the age of each individual patient to be treated, the severity of the infection and other conditions. Generally, however, the active ingredients are administered at a daily dose of 100 mg to 10 g dividedly once to four times a day for preventive or therapeutic purposes.

In an administration example, 2 g (potency) of amoxicillin and 400 mg (potency) of cefixime or 600 mg (potency) of cefdinir are administered each as a daily dose.

The following test examples illustrate the effects of this invention.

TEST EXAMPLE 1

(1) Test Method

Checkerboard method (cf. Hideyo Yamaguchi: "Konnichi no Koseibusshitsu (Antibiotics of today)", page 411, published by Nanzando)

(a) Test Compounds

Cefspan (registered trademark; Fujisawa Pharmaceutical Co.) as CFIX;

Cefzon (registered trademark; Fujisawa Pharmaceutical Co.) as CFDN;

Sawacillin (registered trademark; Fujisawa Pharmaceutical Co.) as AMPC.

(b) Bacterial Strains Used

S. pneumoniae

M. catarrhalis

K. pneumoniae

H. influenzae (c) Method of Determining Minimum Inhibitory Concentration (MIC)

The MIC of each antibiotic used singly and the MIC of each combination of antibiotics were determined by the standard method established by the Japan Society of Chemotherapy, using Mueller-Hinton agar medium (MHA, product of Difco) for M. catarrhalis and K. pneumoniae, 5% equine blood agar (MHA+5% equine blood) for S. pneumoniae, and MHA+5% equine blood (chocolate agar) for H. influenzae. A 100-fold dilution of an overnight culture of each bacterial strain was stamp-inoculated and, after 18 hours of incubation at 37° C. (in the case of S. pneumoniae and H. influenzae, in an atmosphere containing 5% carbon dioxide), the MIC was measured (in $\mu$g/ml)

(2) Test Results

The MIC's of two individual antibiotics and the MIC's of the two respective antibiotics used combinedly were determined by the checkerboard method and the fractional inhibitory concentration index (hereinafter, "FIC index") was determined according to the equation shown below. The results thus obtained are shown in Table 1 to Table 6.

$$FIC\,index = \frac{a}{a_0} + \frac{b}{b_0}$$

$a_o$: MIC of antibiotic A used alone; b: MIC of antibiotic B used alone; a, b: MIC's of antibiotics A and B, respectively, when they are used combinedly.

TABLE 1

Effects of combined use of CFIX and AMPC against penicillin G-resistant S. pneumoniae

| Bacterial | MIC ($\mu$g/ml) | | | | FIC |
|---|---|---|---|---|---|
| | Single use | | Combined use | | |
| strain | CFIX | AMPC | CFIX | AMPC | index |
| FP1884 | 12.5 | 0.2 | 0.78 | 0.05 | 0.31 |
| FP1885 | 6.25 | 0.78 | 0.1 | 0.39 | 0.52 |
| FP1891 | 3.13 | 0.39 | 0.78 | 0.025 | 0.31 |
| FP1906 | 12.5 | 0.76 | 1.56 | 0.2 | 0.38 |

TABLE 2

Effects of combined use of CFIX and AMPC against M. catarrhalis

| Bacterial strain | MIC (μg/ml) | | | | FIC index |
|---|---|---|---|---|---|
| | Single use | | Combined use | | |
| | CFIX | AMPC | CFIX | AMPC | |
| 15007 | 0.05 | 0.78 | 0.0125 | 0.2 | 0.5 |
| 15008 | 0.1 | 0.39 | ≦0.00313 | 0.2 | ≦0.53 |
| 15028 | 0.05 | 3.13 | 0.00625 | 0.78 | 0.38 |

TABLE 3

Effects of combined use of CFIX and AMPC against K. pneumoniae

| Bacterial strain | MIC (μg/ml) | | | | FIC index |
|---|---|---|---|---|---|
| | Single use | | Combined use | | |
| | CFIX | AMPC | CFIX | AMPC | |
| 15004 | 0.05 | 100 | ≦0.00313 | 50 | ≦0.56 |
| 15021 | 0.025 | 25 | 0.0125 | ≦1.56 | ≦0.56 |

TABLE 4

Effects of combined use of CFIX and AMPC against H. influenzae

| Bacterial strain | MIC (μg/ml) | | | | FIC index |
|---|---|---|---|---|---|
| | Single use | | Combined use | | |
| | CFIX | AMPC | CFIX | AMPC | |
| 17004 | 0.5 | 4 | 0.125 | 0.5 | 0.38 |
| 17010 | 0.0625 | 16 | ≦0.0078 | 2 | ≦0.25 |
| 17016 | 0.125 | 16 | 0.0313 | 1 | 0.31 |

TABLE 5

Effects of combined use of CFDN and AMPC against penicillin G-resistant S. pneumoniae

| Bacterial strain | MIC (μg/ml) | | | | FIC index |
|---|---|---|---|---|---|
| | Single use | | Combined use | | |
| | CFDN | AMPC | CFDN | AMPC | |
| FP1884 | 3.13 | 0.2 | 0.2 | 0.05 | 0.31 |
| FP1889 | 12.5 | 0.78 | ≦0.025 | 0.39 | ≦0.5 |
| FP1901 | 6.25 | 0.39 | 0.78 | 0.1 | 0.38 |

TABLE 6

Effects of combined use of CFDN and AMPC against H. influenzae

| Bacterial strain | MIC (μg/ml) | | | | FIC index |
|---|---|---|---|---|---|
| | Single use | | Combined use | | |
| | CFDN | AMPC | CFDN | AMPC | |
| 17030 | 8 | 64 | 2 | 8 | 0.38 |

TABLE 6-continued

Effects of combined use of CFDN and AMPC against H. influenzae

| Bacterial strain | MIC (μg/ml) | | | | FIC index |
|---|---|---|---|---|---|
| | Single use | | Combined use | | |
| | CFDN | AMPC | CFDN | AMPC | |
| 17042 | 1 | 32 | 0.25 | 8 | 0.5 |

TEST EXAMPLE 2

Effect of Combined Use of CFIX and AMPC in a Mixed System Comprising S. Pneumoniae and K. Pneumoniae (human blood simulation system)

Test Method

Precultured bacterial suspensions were diluted to concentration of McFarland 1 in the case of S. pneumoniae and McFarland ½ in the case of K. pneumoniae, and warmed MHA was inoculated with the suspensions each at an inoculum size of 10%. The resulting bacterial suspension was quickly distributed in 200-μl portions into wells of a 96-well plate. After solidification, agar blocks were taken out aseptically and each was placed in a cage (prepared by cutting and boring a syringe tube) in a sample bottle containing 20 ml of 5% serum-containing MHB. After preincubation (37° C., 5% $CO_2$, shake culture, 1 hour), the agar block-containing cage was transferred to a solution corresponding to each serum drug concentration at timed intervals. At the time of sampling, two agar blocks were taken out and homogenized in 5 ml of physiological saline. The bacterial suspension was adequately diluted with MHB and spread on a selective medium. After 20 hours of incubation at 37° C. in the presence of 5% $CO_2$, viable cells were counted.

Bacterial Strains Used

| Bacterial species | Strain No. |
|---|---|
| S. pneumoniae | FP1906 |
| K. pneumoniae | 15004 |

Human blood concentration simulation system:
in the case of administration of CFIX; 200 mg and AMPC; 250 mg Selective medium for viable cell counting:
For S. Pneumoniae; MHA+5% equine serum+AZT (aztreonam) 1 μg/ml
For K. pneumoniae; MHA+VCM (vancomycin) 1 μg/ml Test Results
See FIG. 1.

TEST EXAMPLE 3

Effect of Combined Use of CFIX and AMPC in a Mixed System Comprising S. Pneumoniae and M. catarrhalis (human blood concentration simulation system)

Test Method

Precultured bacterial suspensions were diluted to a concentration of McFarland 1 in the case of S. pneumoniae and McFarland ½ in the case of M. catarrhalis, and warmed MHA was inoculated with the suspensions at inoculum sizes of 10% (S. pneumoniae) and 5% (M. catarrhalis). The resulting bacterial suspension was quickly distributed in 200-μl portions into wells of a 96-well plate. After solidification, agar blocks were taken out aseptically and each was placed in a cage (prepared by cutting and boring a syringe tube) in a sample bottle containing 20 ml of 5% serum-containing MHB. After preincubation (37° C., 5% $CO_2$, shake culture, 1 hour), the agar block-containing cage was transferred to a solution corresponding to each serum drug concentration at timed intervals. At the time of sampling, two agar blocks were taken out and homogenized in 5 ml of physiological saline. The bacterial suspension was adequately diluted with MHB and spread on a selective medium. After 72 hours of incubation at 37° C. in the presence of 5% $CO_2$, viable cells were counted.
Bacterial Strains Used

| Bacterial species | Strain No. |
|---|---|
| S. pneumoniae | FP1906 |
| M. catarrhalis | 15005 |

Human blood concentration simulation system:
   in the case of administration of CFIX; 200 mg and AMPC; 250 mg
Selective medium for viable cell counting:
   For *S. pneumoniae*; MHA+5% equine serum+AZT 10 μg/ml
   For *M. catarrhalis*; MHA+VCM (vancomycin) 1 μg/ml
Test Results
   See FIG. 2.

TEST EXAMPLE 4

Effect of combined used of CFIX and AMPC against mixed respiratory infection with *S. pneumoniae* and *K. pneumoniae* in mice
Test Method
   ICR strain male mice (4 weeks old, 5 animals per group) given cyclophosphamide (200 mg/kg, ip) 4 days prior to infection were nasally infected with *S. pneumoniae* FP1906 ($2.0 \times 10^7$ cfu/mouse) and *K. pneumoniae* 15004 ($5.5 \times 10^3$ cfu/mouse). Each drug was orally administered three times (3, 18 and 26 hours after infection) and, at 2 days after infection, viable cells in the lung were counted.
Test Results

TABLE 7

| | | Viable cells in the lung (logarithm) | |
|---|---|---|---|
| Drug | Dose (mg/kg) | S. pneumoniae | K. pneumoniae |
| Control | 0 | 8.62 | 9.33 |
| CFIX alone | 10 | 8.46*# | 4.14 |
| | 50 | 8.26*# | 2.34 |
| AMPC alone | 10 | 7.04 | 9.32*# |
| | 50 | 5.29* | 9.38*# |
| CFIX + AMPC | 10 + 10 | 6.37 | 3.69 |
| (1:1) combined | 50 + 50 | 2.59 | 1.95 |
| CFIX + AMPC | 5 + 10 | 6.71 | 5.01 |
| (1:2) combined | 25 + 50 | 3.08 | 2.76 |

*Significant difference from CFIX + AMPC (1:1) ($p < 0.01$)
Significant difference from CFIX + AMPC (1:2) ($p < 0.01$)

INDUSTRIAL APPLICABILITY

From the results of Test Example 1, it is evident that the combined use of AMPC and CFIX or CFDN produces a synergistic effect against various bacteria causative of respiratory infections.

From the results of Test Examples 2 to 4, it was found that the combined use of AMPC and CFIX reduced the viable cell counts of both bacterial species in the system of mixed infection with these bacteria as compared with the respective cases of single use.

Therefore, the antimicrobial agent of this invention is useful in the prevention or treatment of not only simple infections with one of various bacteria causative of respiratory infections but also mixed respiratory infections with a plurality of bacterial species, in particular bacteria of the genus Streptococcus (in particular penicillin G-resistant *Streptococcus pneumoniae*) and bacteria belonging to another genus as mentioned above.

The following examples illustrate this invention in further detail.

EXAMPLE 1

(1) Cefixime, amoxicillin, microcrystalline cellulose and hydroxypropylcellulose were thoroughly blended and the mixture was granulated on PharmaMatrix (product of Nara Kikai Seisakusho). The granules were vacuum-dried at 40° C. and subjected to grain size adjustment on a duplex sieve (product of Hata Tekkosho). Magnesium stearate was added to these granules and the resulting mixture was submitted to a P-18 tablet machine (product of Hata Tekkosho), to give plain tablets each having the following composition.
(Plain Tablet Composition)

| Cefixime | 100 mg |
|---|---|
| Amoxicillin | 250 mg |
| Microcrystalline cellulose | 90 mg |
| Hydroxypropylcellulose | 8 mg |
| Magnesium stearate | 2 mg |
| Total | 450 mg |

(2) The plain tablets obtained in (1) were coated with the coating solution specified below on a HiCoater HCT-55 (product of Freund Sangyo) at a feed air temperature of 55° C. and an exhaust gas temperature of 40° C., to give film-coated tablets.
(Coating Solution Composition)

| Hydroxypropylmethylcellulose | 10 mg |
|---|---|
| (Distilled water) | (100 μl) |

EXAMPLE 2

(1) The respective weights given below of cefdinir, amoxicillin, microcrystalline cellulose and hydroxypropylcellulose were thoroughly blended and then granulated on a PharmaMatrix (product of Nara Kikai Seisakusho). The granules were then vacuum-dried at 40° C. and submitted to grain size adjustment on a duplex sieve (product of Hata Tekkosho) for classification, to give fine granules having the following composition.

| | |
|---|---|
| Cefdinir | 25% by weight |
| Amoxicillin | 50% by weight |
| Microcrystalline cellulose | 22% by weight |
| Hydroxypropylcellulose | 3% by weight |

EXAMPLE 3

(1) Cefixime, microcrystalline cellulose and hydroxypropylcellulose were thoroughly blended and the resulting mixture was treated in the same manner as in Example 2 (1) to give fine granules. Hard capsules were filled with the fine granules together with magnesium stearate, to give filled hard capsules each containing the following ingredients in the following amounts.

| | |
|---|---|
| Cefixime | 113 mg (100 mg potency) |
| Microcrystalline cellulose | 135 mg |
| Hydroxypropylcellulose | 10 mg |
| Magnesium stearate | 2 mg |
| Total | 260 mg |

(2) Filled hard capsules each containing the following ingredients in the following amounts were obtained in the same manner as in (1).

| | |
|---|---|
| Amoxicillin | 283 mg (250 mg potency) |
| Microcrystalline cellulose | 75 mg |
| Hydroxypropylcellulose | 10 mg |
| Magnesium stearate | 2 mg |
| Total | 370 mg |

(3) The cefixime-containing hard capsules obtained in (1) were placed and packaged on one side of PTP sheets (5 capsules per sheet) and the amoxicillin-containing hard capsules obtained in (2) on the other side of the same PTP sheets (5 capsules per sheet) to give kits.

EXAMPLE 4

Kits each comprising five cefdinir (100 mg potency)-containing hard capsules placed and packaged on one side of a PTP sheet and five amoxicillin (250 mg potency)-containing hard capsules on the other side of the same PTP sheet were obtained by following the procedures of Example 3 (1) to (3).

BRIEF DESCRIPTION OF THE DRAWINGS

FIG. 2 is a graphic representation of the effect of combined use of CFIX and AMPC in a mixed system comprising *S. pneumoniae* and *M. catarrhalis* (human blood concentration simulation system).

Figure 1C:
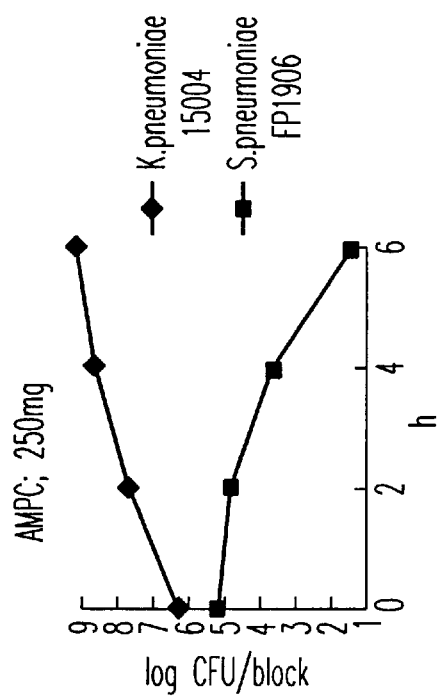
FIG. 1 is a graphic representation of the effect of combined use of CFIX and AMPC in a mixed system comprising *S. pneumoniae* and *K. pneumoniae* (human blood concentration simulation system)
Figure 1D:
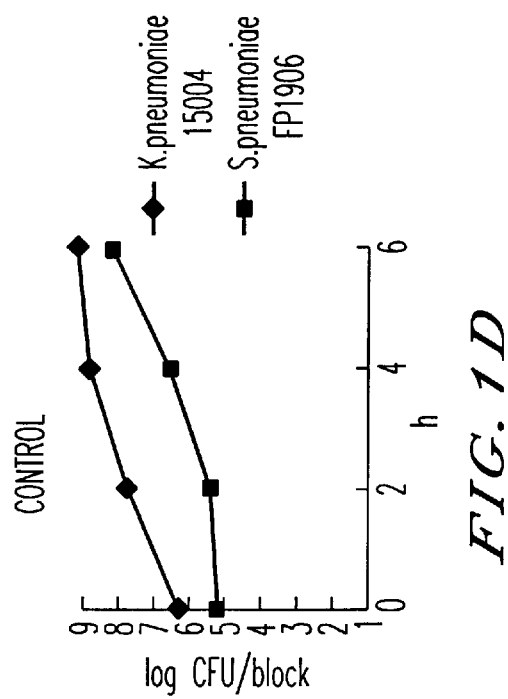
Figure 1A:
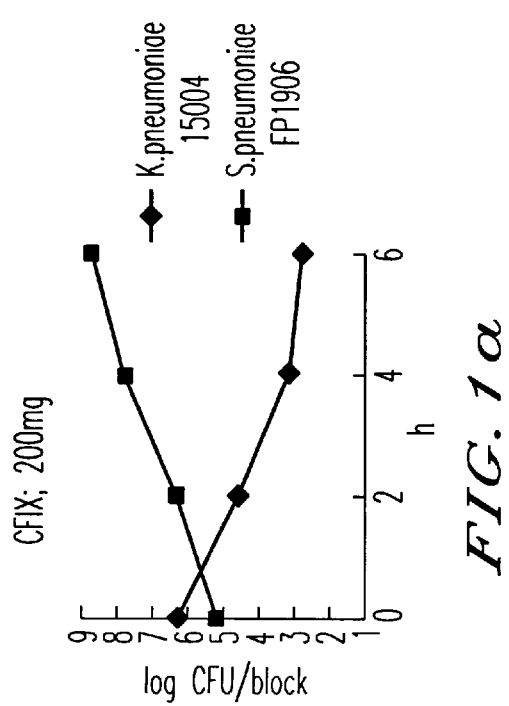
Figure 1B:
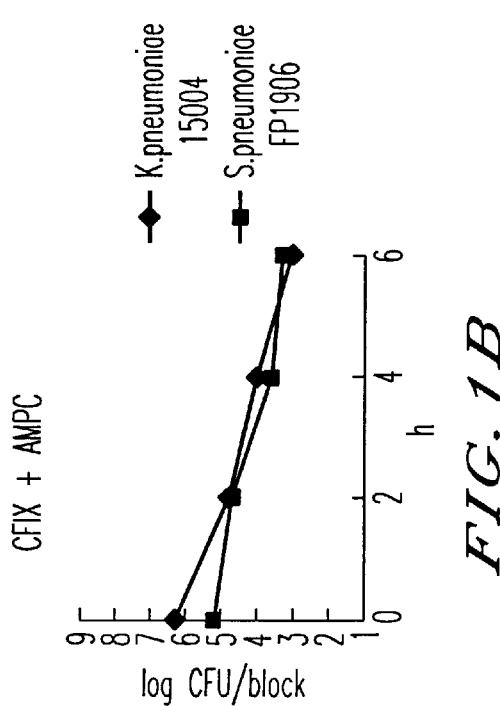

What is claimed is:

1. A method for the prevention or treatment of a mixed respiratory infection, comprising:

administering amoxicillin and cefdinir to a subject suffering from mixed respiratory infection caused by a plurality of genera of bacteria selected from the group consisting of Sreptococcus, Moraxella, Haemophilus and Klebsiella in an amount effective for the prevention or treatment of said mixed respiratory infection.

2. The method of claim 1, wherein the mixed respiratory infection is otitis media, sinusitis, bronchitis or pneumonia.

3. A method for the prevention or treatment of a respiratory infection, comprising:

administering amoxicillin and cefdinir to a patient suffering from a respiratory infection caused by bacteria selected from the group consisting of Streptococcus, Moraxella, Haemophilus and Klebsiella in an amount effective for the prevention or treatment of said respiratory infection.

4. The method of claim 3, wherein the respiratory infection is otitis media, sinusitis, bronchitis or pneumonia.

* * * * *